United States Patent [19]

Nguyen et al.

[11]  4,245,499
[45]  Jan. 20, 1981

[54] APPARATUS FOR THE CONTROLLED SAMPLING OF RAIN WATER

[75] Inventors: Van Dy Nguyen, Jülich; Pavel Valenta, Aachen, both of Fed. Rep. of Germany

[73] Assignee: Kernforschungsanlage Jülich Gesellschaft mit beschränkter Haftung, Jülich, Fed. Rep. of Germany

[21] Appl. No.: 59,122

[22] Filed: Jul. 19, 1979

[30] Foreign Application Priority Data

Jul. 20, 1978 [DE] Fed. Rep. of Germany ....... 2831840

[51] Int. Cl.³ .................... G01W 1/02; G01W 1/14; G01D 9/20
[52] U.S. Cl. ........................... 73/171; 73/189; 346/33 R
[58] Field of Search ............................. 73/171; 346/60

[56] References Cited

U.S. PATENT DOCUMENTS

| 3,162,504 | 12/1964 | Pecknold | 346/23 |
| 3,472,088 | 10/1969 | Ojard | 73/171 |
| 3,485,096 | 12/1969 | Miller | 73/171 |
| 3,826,135 | 7/1974 | Hollmann | 73/171 |
| 3,991,624 | 11/1976 | Davies | 73/189 |
| 4,140,011 | 2/1979 | Krupa et al. | 73/171 |

FOREIGN PATENT DOCUMENTS 1289138  9/1972  United Kingdom ...................... 73/171

Primary Examiner—Daniel M. Yasich
Attorney, Agent, or Firm—Karl F. Ross

[57] ABSTRACT

An apparatus for sampling rain which comprises a container receiving a sampling vessel and provided with a cover having a drive which opens upon detection of a first rain phase and closes at a second rain phase whereby the sampling vessel remains free from contaminants from the atmosphere prior to the rain collection stage.

1 Claim, 1 Drawing Figure

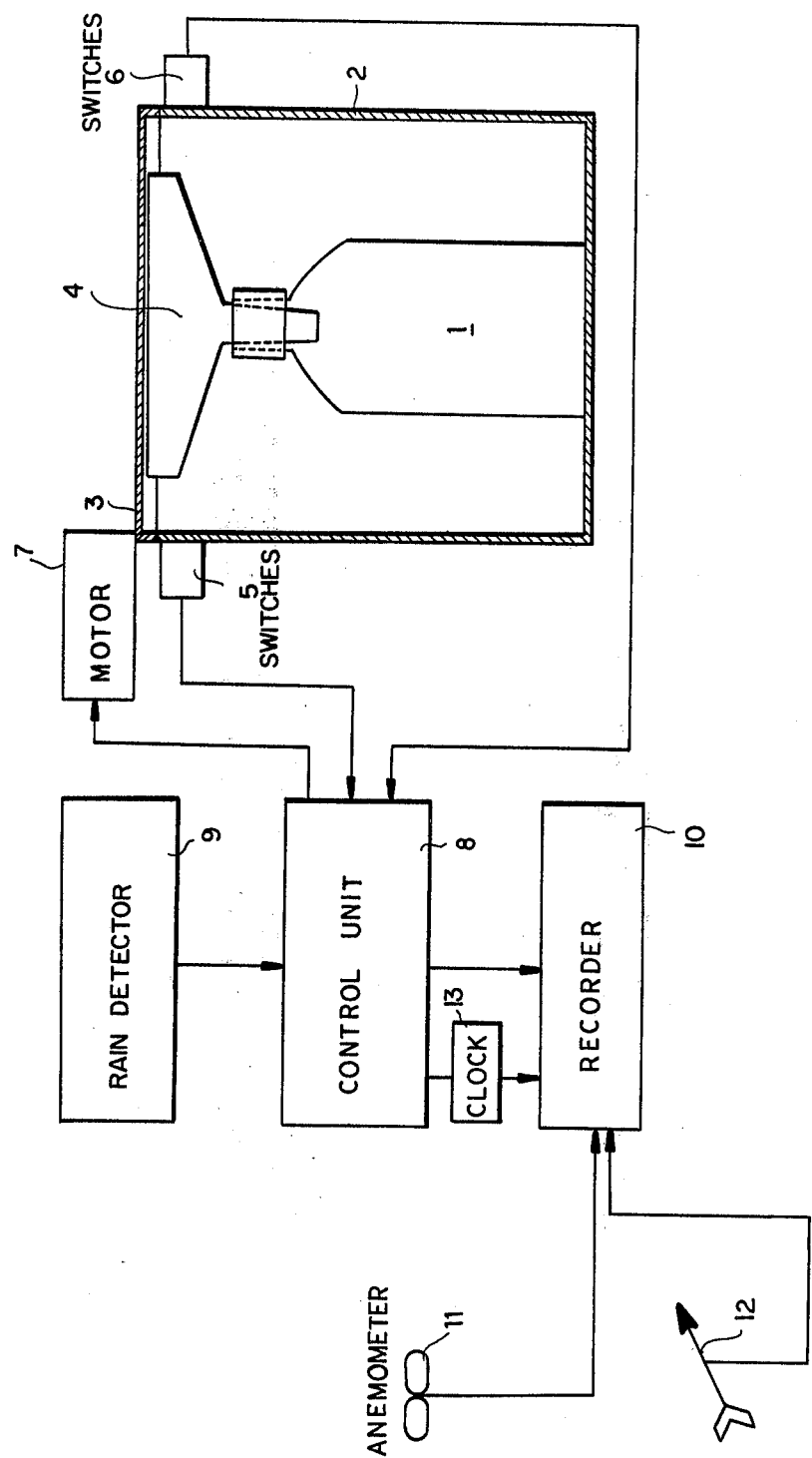

APPARATUS FOR THE CONTROLLED SAMPLING OF RAIN WATER

FIELD OF THE INVENTION

Our present invention relates to an apparatus for the controlled sampling of rain water and, more particularly, to an apparatus for collecting rain water without contamination by particulates from the atmosphere prior to a rain collection operation and for use in the absence of operating personnel.

BACKGROUND OF THE INVENTION

The composition of rain water represents a significant indication of atmospheric contaminants because rain carries such contaminants to the ground.

From ecological studies it is known that substances soluble in rain water are carried to the soil and are picked up by the plant cover, such contaminants including, for example, toxic materials such as heavy metals in solubilized form.

Such contaminants may be released into the atmosphere in the form of dust or aerosols and are picked up by the rain water by mechanical entrainment or solubilization and are carried therewith to the ground. The systematic monitoring of rain water in the environment for potentially toxic, noxious, poisonous or other detrimental materials is of advantage in determining the source of these pollutants and is important in maintaining an environment substantially free therefrom.

To this end, samples are taken of rain water and are analyzed for their impurity contents, generally with the aid of sampling vessels open upwardly and placed at selected locations. The rain water collects in these vessels and then is removed therefrom for analysis.

It has been recognized that it is of advantage to put out such rain water collectors or sampling vessels just before the beginning of a rainfall to avoid contamination of the vessel with dust particles which may otherwise enter the vessel or accumulate therein. However, this poses a problem since weather is often unpredictable and it frequently is not possible to provide operating personnel who can put out the requisite collecting vessel just before the rainstorm in every instance.

Furthermore, it is frequently desired to collect rain water in dependence upon wind strength of direction because the contaminants from a particular direction may afford a greater level of useful information than rain water collected when the wind is blowing from another direction. This has posed an additional stricture upon the individuals responsible for placing the sampling or collecting vessels.

In fact, with existing methods of rain water collection, considerable monitoring of the weather, wind direction and like parameters is required by alert individuals who must always be available or present and frequently, apart from the high cost of operating in this manner, the collection is unsatisfactory.

Note should be taken of the fact that the mean-value results which can be obtained from existing meteorological stations often do not satisfy the requirements as to particularity of collection from rain with the wind blowing from a certain direction. As a practical matter, at least for determining the source of certain types of contamination, it is vital to make the sample collection dependent upon the instantaneous wind speed and the instantaneous wind direction.

OBJECTS OF THE INVENTION

It is, therefore, the principal object of the present invention to provide an improved apparatus capable of automatic sampling of rain water whereby the disadvantages of earlier techniques can be avoided.

Another object of the invention is to provide an automatic sampler for rain water which precludes contamination by dust particles from the environment prior to the onset of rain and which will collect the rain water for a predetermined duration of a rain phase.

Yet another object of the invention is to provide a sampler for the purposes described which can facilitate detection of the source of particular rain contaminants.

SUMMARY OF THE INVENTION

These objects and others which will become apparent are attained in accordance with the present invention in an apparatus for sampling the rain or for the collection of rain water which comprises a container enclosing or forming a sampling or sample-collection vessel and provided with a movable cover which can be shifted by an electrically powered drive between an open position and a closed position. In the closed position, the sampling vessel is closed off from the atmosphere and cannot be contaminated by dust particles from the environment. In the open position a mouth of the sampling vessel is open upwardly to collect rain drops.

According to the invention, electrical control means is provided for operating the drive means, the control means including a detector for the beginning of a rain phase and, advantageously, for the end of a rain phase to generate respective signals which are applied to the drive means for shifting the cover between the open and closed positions.

Thus the signal at the beginning of the rain phase opens the cover and the signal at the end of the rain phase closes the cover.

Naturally, more than one vessel may be provided and, in this case, a plurality, for example four, adjacent vessels are used and are provided with a common cover, advantageously being disposed within a single container.

According to a further feature of the invention, the rain detector is in an electric circuit with a registering or recording device which registers or records signals representing the wind direction from a wind-direction sensor or detector. The recording device is placed in operation at the beginning of the rain phase by an output signal from the rain detector and is cut off at the end of the rain phase by the terminal signal therefrom.

According to another feature of the invention, a registering or recording device is provided for the wind speed, this recording device being likewise started by the start signal from the rain detector and stopped by the terminate signal from the rain detector.

This device can receive an input from a wind-speed sensor or detector (anemometer).

Advantageously the wind speed and wind-direction recorders can be combined in a single two-channel recorder plotting the wind speed and wind direction as a function of time, i.e. a two-channel (signal vs. time) graphic recorder.

It has also been found to be advantageous to include in the circuitry for the rain detector, a timer which registers the beginning and end of the rain phase. This clock can also be integrated in the recording device mentioned above.

The apparatus of the present invention thus enables automatic monitoring at a predetermined location of the release of toxic agents into the environment from a particular source or enables the determination of a source by analysis of the collected rain water. The arrangement of several such devices in particular spaced orientation in a network provides a systematic regional monitoring of the environment effects of a toxic-agent source.

BRIEF DESCRIPTION OF THE DRAWING

The above and other objects, features and advantages of the present invention will become more readily apparent from the following description, reference being made to the accompanying drawing of which the sole FIGURE is a diagram illustrating the apparatus of the present invention.

Specific Description

As can be seen from the drawing, the apparatus of the present invention comprises a container 2 receiving a sampling vessel 1 and provided at its upper end with a cover 3 which is driven by a motor 7 means mounted on the container 2. The container 2 is so dimensioned that it has room for both the vessel 1 and its funnel 4.

The cover 3 may be pivotally connected to the container so as to be swung upwardly by the motor 7 in any conventional manner.

The motor 7 is operated by a control unit 8 which may be a microprocessor and responds to start and terminate signals from a rain detector 9 which can be of any conventional moisture-sensing type. The start signal from the rain detector 9 is supplied to the control unit which initiates operation of the motor 7 upon the initial detection of rainfall to open the cover 3 and allow the rain drops to collect in the vessel 1. When further rainfall is no longer detected, the signal from the detector terminates and the control unit reverses the motor 7 to close the cover 3.

The output of the control unit 8 is also applied to a recorder 10 which is connected to an anemometer 11 providing an input representing wind velocity to the recorder and to a wind direction sensor 12 likewise providing an input to the recorder 10.

The recorder 10 is started and stopped by the control unit at the beginning and ending of the rain phase and records wind speed from the anemometer and wind direction from unit 12 over this interval. A clock 13 is likewise started and stopped by the control unit at these points to print on the recording strip of the recorder the starting time and stopping time of the rain collection phase.

A pair of switches 5 and 6 signal the completely open and completely closed stations of the cover to the control unit to turn off the motor when the cover has reached its fully open and fully closed positions respectively.

As soon as the first rain drops come into contact with the rain detector 9, the signal applied by the latter to the control unit 8 turns on the motor 7 to raise the cover. Simultaneously, the recorder 10 is energized and the clock 13 prints on the recording strip the starting time. The wind velocity and wind direction measurements are recorded. When the cover reaches its maximum open position, switch 5 operates to terminate the drive of the motor and rain collection continues until the end of rainfall when the signal from the detector 9 causes the control unit 8 to reverse the motor 7 and swing the cover 3 into its closed position. This signal also stops the recorder and induces the clock 13 to print out the time at which stoppage occurred. The switch 6 shuts off the motor when the cover is fully closed.

The sensitive surface of the rain detector can be heated to prevent moisture from the atmosphere, which is not in the form of rain, from increasing the length of the collection interval. The moisture on the surface is thus evaporated immediately after the termination of the rain phase.

SPECIFIC EXAMPLE

The apparatus of the present invention was tested with a vessel 1 in the form of a polyethylene bottle having a capacity of 5 liters. The container 2 was a rectangular parallelepipedal box of dimensions of $600\times600\times600$ mm composed of polyacrylate resin and provided with an aluminum cover 3. The funnel 4 had a diameter of 250 mm and was composed of polyethylene.

The rain detector was a rain sensor of type 1515 of the firm of LAMBRECHT, Göttingen, Germany.

The drive motor 7 was a DC motor operating at 24 volts and 4000 RPM with a stepdown gearing. The recorder was a two-channel X-t recorder of the paper tape type, one channel registering the wind direction and the other channel the wind velocity on the paper strip. The time determination of the rain phase was applied to the tape or was determined by the feed of the paper tape which was not turned off at the end of a rain phase.

We claim:

1. An apparatus for the controlled sampling of rain comprising:

- a sampling vessel having an upwardly open mouth adapted to receive rain drops;
- a cover disposed so as to be shiftable between a first position closing said vessel and a second position wherein said vessel is open to receive rain;
- first and second signalling means on said vessel to signal when each of said positions is reached;
- a motor connected to said cover and electrically energizable by signal receiving means responsive to said signalling means so as to displace said cover between said first and second positions;
- a rain detector responsive to the onset and termination of a rain phase and exposed to the atmosphere for producing at least one signal upon the onset of rain and upon the termination of a rain phase;
- circuitry between said detector and said motor responsive to said signal for energizing said motor at the onset of a rain phase and closing said cover at the conclusion of a rain phase;
- a recorder connected to said circuitry and placed in operation upon the onset of said rain phase;
- clock means for registering the time of onset of said rain phase and of termination thereof, said clock means being connected to said circuitry;
- a wind-direction sensor connected to said recorder for recording thereon the wind direction upon the onset of said rain phase; and
- a wind-speed sensor connected to said recorder for recording thereon the wind speed upon the onset of said rain phase, said recorder being two-channel recorder recording the wind speed and wind direction as a function of time of collection of rain by said vessel.

* * * * *